(12) United States Patent
Takezawa et al.

(10) Patent No.: US 7,842,702 B2
(45) Date of Patent: Nov. 30, 2010

(54) TREATMENT FOR IRRITABLE BOWEL SYNDROME

(75) Inventors: Ryuichi Takezawa, Chuo-ku (JP); Hitoshi Doihara, Chuo-ku (JP); Hiroyuki Ito, Chuo-ku (JP); Jotaro Suzuki, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/027,564

(22) Filed: Feb. 7, 2008

(65) Prior Publication Data

US 2008/0188512 A1 Aug. 7, 2008

(30) Foreign Application Priority Data

Feb. 7, 2007 (JP) .............................. 2007-028282

(51) Int. Cl.
*A61K 31/4375* (2006.01)
(52) U.S. Cl. ...................................... 514/306
(58) Field of Classification Search ....................... None
See application file for complete search history.

(56) References Cited

U.S. PATENT DOCUMENTS

2005/0192329 A1 9/2005 Nishida et al.

FOREIGN PATENT DOCUMENTS

| EP | 0 157 346 A2 | | 10/1985 |
|---|---|---|---|
| EP | 0 811 378 A1 | | 12/1997 |
| JP | 6-256187 | | 9/1994 |
| WO | WO 94/07491 | | 4/1994 |
| WO | WO 95/21611 | | 8/1995 |
| WO | WO2004062623 | * | 7/2004 |
| WO | WO 2006/122069 A2 | | 11/2006 |

OTHER PUBLICATIONS

Vippagunta et al., Advanced Drug Delivery Reviews, 48 (2001), pp. 3-26.*

T. Imai, et al., "Effects of a novel orally-active antiallergic drug, quinotolast (FK021), on airway clearance, Nippon yakurigaku zasshi" Folia Pharmacologica Japonica, vol. 104, No. 4, 1994, pp. 347-355 (with English abstract and a partial English translation).
Javier Santos, et al., "Targeting mast cells in the treatment of functional gastrointestinal disorders", Current Opinion in Pharmacology, vol. 6, No. 6, 2006, pp. 541-546.
Susan K. Hadley, et al., "Treatment of Irritable Bowel Syndrome", American Family Physician, vol. 72, No. 12, Dec. 15, 2005, pp. 2501-2506.
C. Lunardi, et al., "Double-Blind Cross-Over Trial of Oral Sodium Cromoglycate in Patients With Irritable Bowel Syndrome Due to Food Intolerance", Clinical and Experimental Allergy, vol. 21, 1991, pp. 569-572.
G. F. Stefanini, et al., "Oral Disodium Cromoglycate Treatment on Irritable Bowel Syndrome: An Open Study on 101 Subjects With Diarrheic Type", The American Journal of Gastroenterology, vol. 87, No. 1, 1992, pp. 55-57.
G. F. Stefanini, et al., "Oral Cromolyn Sodium in Comparison With Elimination Diet in the Irritable Bowel Syndrome, Diarrheic Type", Scandinavian Journal of Gastroenterology, vol. 30, 1995, pp. 535-541.
Jun-Ho La, et al., "Role of Mucosal Mast Cells in Visceral Hypersensitivity in a Rat Model of Irritable Bowel Syndrome", Journal of Veterinary Science, vol. 5, No. 4, 2004, pp. 319-324.
Katsumasa Kobayashi, et al., "Effects of Quinotolast, A New Orally Active Antiallergic Drug, on Experimental Allergic Models", Japanese Journal of Pharmacology, vol. 63, 1993, pp. 73-81.
T. Mori, et al., "Pro-drugs for the Oral Delivery of Disodium Cromoglycate", vol. 36 (1), pp. 338-344 (1988).
L. Ramos, et al., AGA Abstracts, Abstract No. 325, p. A-60-A61 (2007).
S.D. Kuiken et al., *Aliment. Pharmacol. Ther.*, vol. 22, pp. 157-164 (2005).
I. Posserud et al., *Gastroenterology*, vol. 133, pp. 1116-1123 (2007).

* cited by examiner

*Primary Examiner*—Phyllis G. Spivack
(74) *Attorney, Agent, or Firm*—Oblon, Spivak, McClelland, Maier & Neustadt, L.L.P.

(57) ABSTRACT

N-(1H-tetrazol-5-yl)-1-phenoxy-4H-quinolizin-4-one-3-carboxamide is effective for treating IBS. In addition, IBS may be effectively treated with N-(1H-tetrazol-5-yl)-1-phenoxy-4H-quinolizin-4-one-3-carboxamide when used concomitantly with at least one of various serotonin 5-HT3 receptor antagonists.

20 Claims, 5 Drawing Sheets

TREATMENT FOR IRRITABLE BOWEL SYNDROME

CROSS REFERENCES TO RELATED APPLICATIONS

This application claims priority to Japanese Patent Application No. 2007-028282 filed Feb. 7, 2007, the content of which is incorporated herein by reference in its entirety.

BACKGROUND OF THE INVENTION

1. Field of the Invention

The present invention relates to agents for treating irritable bowel syndrome. The present invention also relates to methods for treating irritable bowel syndrome.

2. Discussion of the Background

Irritable bowel syndrome (IBS) is a functional bowel disorder in which abdominal pain or discomfort is associated with defecation or a change in bowel habit, and with features of disordered defecation. This disorder is not accompanied by organic disorders whose symptoms can be explained (e.g., inflammation, tumor and the like), but the result of the functional abnormality of lower digestive tracts. The symptoms are long-lasting or come and go over time. According to the Rome III published in 2006 (*Gastroenterology*, 2006, vol. 130, pp. 1480-1491), IBS is classified based on the predominant stool pattern into four subtypes of IBS with diarrhea (IBS-D), IBS with constipation (IBS-C), mixed IBS (IBS-M) which shows both diarrhea and constipation, and unsubtyped IBS (IBS-U). Though IBS is not a fatal disease, it has been found that it causes difficulty for patients in carrying out social activities because they undergo behavioral restriction depending on the symptoms. The prevalence of IBS in the general population is estimated from 10% to 15% in North America, Europe and Asia, and its annual morbidity rate is from 1% to 2%. In addition, IBS is a highly frequent disorder occupying from 20 to 50% of the gastrointestinal outpatients. Its male to female ratio is predominant in female because it is 1:2 regardless of the human race, and it has higher prevalence rate in the younger generation.

Since mental or physical stress is strongly implicated in the onset of the symptom of IBS, it is regarded as a stress-related disease. Actually, it is known that emotional stress worsens the symptoms of IBS patients.

As the drug therapy of IBS, anticholinergics or tricyclic antidepressants are used for abdominal pain/discomfort, and conventional anti-diarrheal drugs or laxatives are used for diarrhea or constipation, respectively, but they are merely symptomatic treatments and their effects are not clear. Polycarbophil calcium is an agent whose effects can be expected for both diarrhea and constipation in Japan, but the efficacy is very limited because not only there is an abdominal swelling feeling at the initial stage of its administration but also it requires time for expressing the effects. Minor tranquilizers and antidepressants are used when anxiety and tension are considerably increased due to stress, but they are administered at a relatively lower doses, so that their effects are also limited. As described above, a sufficiently effective therapeutic method for IBS has not been established.

A 5-HT3 receptor antagonist, alosetron, and a 5-HT4 receptor agonist, tegaserod, are medical agents for IBS-D and IBS-C, respectively. These agents improve bowel movement by regulating movement of intestines, and the onset of effect is quick. However, alosetron shows only an improvement rate of about 50% for abdominal symptoms and diarrhea, constipation occurs in 30 to 35% of the patients and it causes ischemic colitis (including fatal cases) as a serious side effect, so that its use is limited. As in the case of alosetron, the efficacy of tegaserod is not sufficient, and the use of tegaserod is also limited to severe IBS patients because of its risk for cardiovascular side effects. Accordingly, it is considered that the need for an IBS-treating agent remains unmet.

In recent years, it has been reported that micro-inflammation, infection, or allergy in the intestinal tracts are also important as risk factors of IBS, in addition to the mental and physical stresses. It has been considered classically that the mast cells are activated only by an antigenic stimulation, but it is now considered the cells are activated also by a stress, a micro-inflammation and nervous system mediators. The activation of mast cells induces the release of granular mediators such as histamine, lipid mediators, and cytokines that can modulate intestinal functions. These mechanisms have been recently assumed to impact to the pathogenesis of IBS.

Under such circumstances, there are the following reports suggesting the effects of mast cell degranulation inhibitors.

*Clinical and Experimental Allergy*, 1991, vol. 21, pp. 569-572; *The American Journal of Gastroenterology*, 1992, vol. 87 (1), pp. 55-57; and *Scandinavian Journal of Gastroenterology*, 1995, vol. 30, pp. 535-541 disclose that a mast cell degranulation inhibitor, sodium cromoglycate (cromolyn), was effective when administered at a dose of from 1,500 to 2,000 mg per day to specific IBS patients having food allergy.

*Journal of Veterinary Science*, 2004, vol. 5 (4), pp, 319-324 discloses that doxantrazole which has a mast cell degranulation inhibitory activity is effective for rat intestinal hyperesthesia.

Also, International Publication WO 95/21611 discloses that a histamine $H_1$ antagonist ketotifen inhibited the secretion of rat mast cell protease II (RMCPII). International Publication WO 95/21611 discloses that sodium cromoglycate is classified as a phosphatase inhibitor and not included in the disclosed invention though it has the mast cell degranulation inhibitory activity. Moreover, though a great variety of compounds including an anti-female hormone agent and a histamine $H_3$ antagonist are defined as mast cell degranulation inhibitors in addition to a histamine $H_1$ antagonist, their inhibitory activity of mast cell degranulation are unknown. So that it cannot be said that this reference clarifies whether or not the mast cell degranulation inhibitors other than histamine $H_1$ antagonists are effective for the treatment of IBS.

On the other hand, it has been reported that N-(1H-tetrazol-5-yl)-1-phenoxy-4H-quinolizin-4-one-3-carboxamide has mast cell degranulation inhibitory activity (see, *Japanese Journal of Pharmacology*, 1993, vol. 63, pp. 73-81) and is effective for the treatment of allergy and ulcer (see, EP-0 157 346 A), cough and phlegm (see, JP-A-6-256187), pain, conjunctivitis and rheumatoid arthritis (see, International Publication WO 94/07491) and interstitial pneumonia, inflammatory bowel disease and vascular hypertrophy (see, EP-0811378 A), but its effects for IBS have not been reported.

Thus, there remains a need for agents and methods which are effective for treating IBS.

SUMMARY OF THE INVENTION

Accordingly it is one object of the present invention to provide novel IBS-treating agents.

It is another object of the present invention to provide novel methods for treating IBS.

These and other objects, which will become apparent during the following detailed description, have been achieved by the inventors' discovery that N-(1H-tetrazol-5-yl)-1-phenoxy-4H-quinolizin-4-one-3-carboxamide is effective as an IBS-treating agent and the inventors' further discovery that superior IBS-treating effect can be obtained by the concomitant use of this compound with at least one of the various 5-HT3 receptor antagonists, thereby accomplishing the present invention.

That is, the present invention provides the following.

(1) A method for treating IBS, which comprises administering an effective amount of N-(1H-tetrazol-5-yl)-1-phenoxy-4H-quinolizin-4-one-3-carboxamide, a pharmaceutically acceptable salt thereof or a solvate thereof to a patient in need thereof.

(2) An agent for treating IBS, which comprises combination of N-(1H-tetrazol-5-yl)-1-phenoxy-4H-quinolizin-4-one-3-carboxamide, a pharmaceutically acceptable salt thereof or a solvate thereof with at least one 5-HT3 receptor antagonist.

(3) A method for treating IBS, which comprises administering effective amounts of N-(1H-tetrazol-5-yl)-1-phenoxy-4H-quinolizin-4-one-3-carboxamide, a pharmaceutically acceptable salt thereof or a solvate thereof and at least one 5-HT3 receptor antagonist to a patient in need thereof.

(4) A composition, comprising:
 (a) N-(1H-tetrazol-5-yl)-1-phenoxy-4H-quinolizin-4-one-3-carboxamide, a pharmaceutically acceptable salt thereof, or a solvate thereof; and
 (b) at least one 5-HT3 receptor antagonist.

(5) The agent, method, or composition of the aforementioned (2) to (4), wherein the at least one 5-HT3 receptor antagonist is an agent selected from the group consisting of ramosetron, alosetron, and a mixture thereof.

(6) The agent, method, or composition of the aforementioned (2) to (4), wherein the at least one 5-HT3 receptor antagonist is ramosetron.

(7) The agent, method, or composition of the aforementioned (1) to (6), wherein the N-(1H-tetrazol-5-yl)-1-phenoxy-4H-quinolizin-4-one-3-carboxamide, a pharmaceutically acceptable salt thereof or a solvate thereof is sodium salt monohydrate of N-(1H-tetrazol-5-yl)-1-phenoxy-4H-quinolizin-4-one-3-carboxamide.

(8) The agent, method, or composition of the aforementioned (1) to (7), wherein the IBS is IBS with diarrhea.

(9) The agent, method, or composition of the aforementioned (1) to (7), wherein the IBS is IBS with constipation.

(10) The agent, method, or composition of the aforementioned (1) to (7), wherein the IBS is mixed IBS.

The N-(1H-tetrazol-5-yl)-1-phenoxy-4H-quinolizin-4-one-3-carboxamide as an active ingredient of the pharmaceutical preparations of the present invention is useful as an IBS-treating agent and further useful as an IBS-treating agent when said compound is combined with a 5-HT3 receptor antagonist.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 9A shows the effects of compound 1, and FIG. 9B shows the effects of doxantrazole, respectively (N=10). In this connection, the ordinate axis in each graph shows the number of spontaneous defecation for 2 hours after the initiation of the experiments. The dosage units on the abscissa axis are all mg/kg. The symbol * in FIG. 9B means death of all cases.

DETAILED DESCRIPTION OF THE PREFERRED EMBODIMENTS

Figure 1:
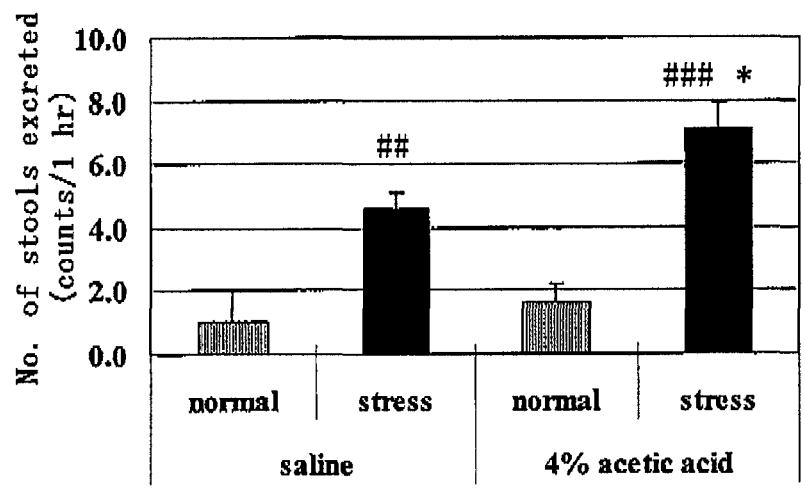
FIG. 1 is a graph showing restraint stress-induced defecation in the acetic acid-induced IBS model in the agent-nonadministered group in Example 2 (N=5 to 10). The ordinate axis in the graph shows the number of stools excreted for 1 hour after the initiation of restraint stress. The symbols ## and ### show a P value of <0.01 and <0.001, respectively, in the restrained group compared to the unrestrained group, and the symbol * shows a P value of <0.05 in the 4% acetic acid-treated group compared to the physiological saline-treated group in the restrained group (Student's t-test).

N-(1H-tetrazol-5-yl)-1-phenoxy-4H-quinolizin-4-one-3-carboxamide is disclosed in EP-0 157 346 A, JP-A-6-256187, International Publication WO 94/07491, and EP-0 811 378 A and exists in various forms of salts and solvates, and these can be further present in various polymorphic forms. For example, it may exist as a salt with inorganic bases (e.g., sodium, potassium, magnesium, calcium, aluminum and the like) or with organic bases (e.g., methylamine, ethylamine, ethanolamine, lysine, ornithine and the like) can be present. As the active ingredient of the agent of the present invention, it may be in any form but is preferably sodium salt monohydrate of N-(1H-tetrazol-5-yl)-1-phenoxy-4H-quinolizin-4-one-3-carboxamide (also referred to in this specification as "compound 1") and is particularly preferably the crystalline form disclosed in JP-A-1-104073. The compound can be prepared by the method described in the above Patent References, JP-A-62-77385 and JP-A-63-284174, as well.

The term "IBS" includes IBS with diarrhea (IBS-D), IBS with constipation (IBS-C), mixed IBS (IBS-M), and un-subtyped IBS (IBS-U) according to Rome II. Preferred are IBS with diarrhea (IBS-D), IBS with constipation (IBS-C), and mixed IBS (IBS-M), more preferred are IBS with diarrhea (IBS-D) and IBS with constipation (IBS-C), and further preferred is IBS with diarrhea (IBS-D).

The term "treatment of IBS" includes administration of an agent for the purpose of alleviating or eliminating symptoms when diarrhea, constipation and/or abdominal discomfort are found in a patient whose contraction of IBS or a possibility thereof was confirmed by diagnosis, or for the purpose of suppressing symptoms before onset of the disease when they are predicted.

The term "abdominal discomfort" includes abdominal pain, malaise-like uncomfortable feelings due to visceral hypersensitivity, altered bowel motility, or other factors.

The term "5-HT3 receptor antagonist" includes compounds generally reported as 5-HT3 receptor antagonists such as ramosetron, alosetron, granisetron, ondansetron, azasetron, tropisetron, dolasetron, cilansetron, and the like, in which ramosetron or alosetron are preferable, and ramosetron is more preferable.

As the "agent for treating IBS, which comprises a combination of N-(1H-tetrazol-5-yl)-1-phenoxy-4H-quinolizin-4-one-3-carboxamide, a pharmaceutically acceptable salt thereof or a solvate thereof with a 5-HT3 receptor antagonist" of the present invention, it includes a pharmaceutical composition (medical mixture) for the treatment of IBS, which comprises an effective amount of N-(1H-tetrazol-5-yl)-1-phenoxy-4H-quinolizin-4-one-3-carboxamide, a pharmaceutically acceptable salt thereof or a solvate thereof and an effective amount of a 5-HT3 receptor antagonist as well as a kit which comprises two pharmaceutical preparations having an IBS-treating agent as a first preparation containing N-(1H-tetrazol-5-yl)-1-phenoxy-4H-quinolizin-4-one-3-carboxamide, a pharmaceutically acceptable salt thereof or a solvate thereof as the active ingredient and another IBS-treating agent as a second preparation containing a 5-HT3 receptor agonist as the active ingredient. In this case, the two pharmaceutical preparations are administered simultaneously or separately through the same route or different routes of administration.

The term "kit which comprises two pharmaceutical preparations" comprises two pharmaceutical preparations containing respective active ingredients in such a combination that it can be used in the concomitant use of these active ingredients, and its examples include a package which may contain a supplementary preparation and a display member for facilitating administration of placebo and the like by adjusting respective administration periods as occasion demands. In addition, the "simultaneously" means that the first preparation and the second preparation are administered simultaneously through the same route of administration, and the "separately" means that the first preparation and the second preparation are administered separately through the same route or different routes of administration at the same or different administration frequencies or administration intervals. Desirably, by taking bioavailability, stability, and the like of respective preparations into consideration, they are administered simultaneously or separately under the preparation formulation, route of administration, administration frequency and the like administration conditions suited for respective preparations.

The term "solvate" includes solvates of any kind of solvent as far as which can be pharmaceutically acceptable, e.g. ethanol, water, and the like, preferably water.

The IBS-treating agent of the present invention can be prepared as a pharmaceutical preparation which contains N-(1H-tetrazol-5-yl)-1-phenoxy-4H-quinolizin-4-one-3-carboxamide as its active ingredient, or further contains a 5-HT3 receptor antagonist, by using carriers, excipients and the like for pharmaceutical preparations which are generally used in this field.

The administration may be either oral administration by tablets, pills, capsules, granules, powders, solutions and the like or parenteral administration by injections for intraarticular injection, intravenous injection, intramuscular injection and the like, suppositories, eye drops, eye ointments, transdermal solutions, ointments, transdermal patches, transmucosal solutions, transmucosal patches, inhalations and the like.

As the solid composition for oral administration by the present invention, tablets, powders, granules and the like may be used. In such a solid composition, one or more active substances may be mixed with at least one inert filler such as lactose, mannitol, glucose, hydroxypropylcellulose, microcrystalline cellulose, starch, polyvinyl pyrrolidone and/or aluminum magnesium metasilicate or the like. In accordance with the usual way, the composition may contain inert additives such as lubricants, e.g. magnesium stearate and the like, disintegrators, e.g. carboxymethylstarch sodium and the like, stabilizers and solubilizing agents. As occasion demands, the tablets or pills may be coated with a sugar coating or a film of a gastric or enteric substance.

As the liquid composition for oral administration, pharmaceutically acceptable emulsions, solutions, suspensions, syrups, elixirs, and the like are included, and generally used inert diluents such as purified water, ethanol and the like can be used. In addition to the inert diluents, said liquid composition may contain auxiliary agents, such as solubilizing agents, moistening agents, suspending agents, flavors, sweeteners, correctives, aromatics, and antiseptics.

As the injections for parenteral administration, sterile aqueous or non-aqueous solutions, suspensions, and emulsions are included. As the aqueous solvent, for example, distilled water for injection and physiological saline are included. Examples of the non-aqueous solvent include propylene glycol, polyethylene glycol, vegetable oil (e.g. olive oil), alcohols (e.g. ethanol), polysorbate 80 (the name in *Japanese Pharmacopeia*), and the like. Such a composition may further contain tonicity agents, antiseptics, moistening agents, emulsifying agents, dispersing agents, stabilizing agents, solubilizing agents, or solubilizing agents. These are sterilized by, for example, filtration through a bacteria retaining filter, formulation of germicides, or irradiation. In addition, these can also be used by producing sterile solid compositions and dissolving or suspending them in sterile water or a sterile solvent for injection prior to use.

Transmucosal preparations, such as inhalations, transnasal preparations may be used in the form of solid, liquid, or semisolid, and can be produced in accordance with the conventionally known methods. For example, conventionally known fillers and also pH adjusting agents, antiseptics, surfactants, lubricants, stabilizers, thickeners, and the like may be optionally added. An appropriate device for inhalation or blowing can be used for the administration. For example, a compound can be administered as such or as a powder of formulated mixture, or as a solution or suspension in combination with a medically acceptable carrier, by using a metered dose inhalation device or the like conventionally known device or a sprayer. The dry powder inhaler or the like may be for single or multiple administration use, and a dry powder or powder-containing capsule can be used. Alternatively, it may be in the form of a pressurized aerosol spray or the like which uses an appropriate propellant such as chlorofluoroalkane, hydrofluoroalkane, carbon dioxide, or a like suitable gas.

In the case of oral administration, the daily dosage is suitably approximately from 0.01 to 10 mg/kg of body weight, preferably from 0.1 to 1 mg/kg of body weight, in terms of N-(1H-tetrazol-5-yl)-1-phenoxy-4H-quinolizin-4-one-3-carboxamide, and this may be administered once or by dividing into two doses. When administered intravenously, the daily dosage is suitably approximately from 0.001 to 10 mg/kg of body weight in terms of N-(1H-tetrazol-5-yl)-1-phenoxy-4H-quinolizin-4-one-3-carboxamide, and this may be administered once a day or by dividing it into two or more times per day. In addition, in the case of a transmucosal preparation, the daily dosage is suitably approximately from 0.01 to 10 mg/kg of body weight in terms of N-(1H-tetrazol-5-yl)-1-phenoxy-4H-quinolizin-4-one-3-carboxamide, and may be administered once a day or by dividing the daily dosage into two or more doses. The dosage is optionally decided in response to each individual case by taking symptom, age, sex, and the like into consideration.

With respect to the 5-HT3 receptor antagonist, known administration routes and dosages may be applied. For example, in case of ramosetron, the dosage disclosed in US 2005/0192329 A1, which is incorporated herein by reference in its entirety, may be used. Concretely, the dose may suitably be approximately 0.001 to 0.05 mg/day, preferably 0.002 to 0.02 mg/day, for oral administration as ramosetron hydrochloride.

The N-(1H-tetrazol-5-yl)-1-phenoxy-4H-quinolizin-4-one-3-carboxamide as the active ingredient of the present invention can be used concomitantly with a 5-HT3 receptor antagonist or other various IBS-treating agents. Said concomitant use preparations may be administered simultaneously, separately continuously or at desired intervals. The simultaneous administration preparation may be a combination drug or made into separate preparations.

In the case of a composition which contains both (a) N-(1H-tetrazol-5-yl)-1-phenoxy-4H-quinolizin-4-one-3-carboxamide, a pharmaceutically acceptable salt thereof, or a solvate thereof; and (b) at least one 5-HT3 receptor antagonist, the weight ratio of (a) N-(1H-tetrazol-5-yl)-1-phenoxy-4H-quinolizin-4-one-3-carboxamide, a pharmaceutically acceptable salt thereof, or a solvate thereof and the (b) at least one 5-HT3 receptor antagonist is suitably selected. For example, in the case of N-(1H-tetrazol-5-yl)-1-phenoxy-4H-quinolizin-4-one-3-carboxamide sodium salt monohydrate: ramosetron hydrochloride, the weight ratio is preferably 10:1 to 100,000:1, more preferably 100:1 to 10,000:1.

Other features of the invention will become apparent in the course of the following descriptions of exemplary embodiments which are given for illustration of the invention and are not intended to be limiting thereof.

EXAMPLES

In the following examples, N-(1H-tetrazol-5-yl)-1-phenoxy-4H-quinolizin-4-one-3-carboxamide is referred to "compound 1".

Example 1

Preparation of Acetic Acid-Induced IBS Model

Preparation of an IBS model was carried out by the following method with reference to the method of Jun-Ho La et al. (*World J. Gastroenterol.*, 2003, vol. 9 (12), pp. 2791-2795). Male Sprague-Dawley (SD) rats or Wistar rats after an overnight fast were used. Colitis was induced by intracolonic instillation of 1 ml 4% acetic acid at 8 cm proximal to the anus for 30 seconds under light ether anesthesia. Then, 1 ml physiological saline was instilled to dilute the acetic acid and flush the colon twice. Rats were recovered from colitis for 6 days, and used for experiments shown in Examples 2 and 3 at 7 days after induction of colitis as "IBS rat (4% acetic acid)". In addition, rats received physiological saline instead of acetic acid was used as a "control group (saline)".

In this connection, it was confirmed that the activity of myeloperoxidase (MPO) which is an index of intestinal inflammation increases 1 to 2 days after intracolonic instillation of acetic acid, but the MPO activity returns to the same level of the control group and the inflammation image is not observed also 7 days thereafter.

Example 2

Restraint Stress-Induced Defecation in Rats

Figure 2:
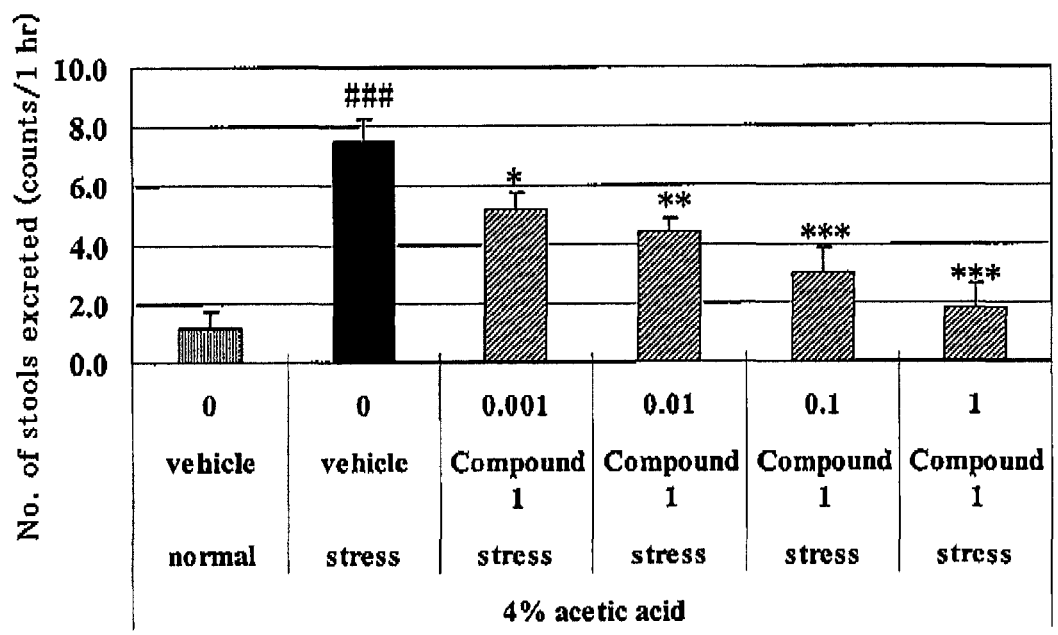
FIG. 2 is a graph showing effects of compound 1 on restraint stress-induced defecation in the acetic acid-induced IBS model in Example 2 (N=6 to 10). The ordinate axis in the graph shows the number of stools excreted for 1 hour after the initiation of restraint stress. The dosage units on the abscissa axis are all mg/kg. The symbol ### shows a P value of <0.001 in the restrained group compared to the unrestrained group (Student's t-test), and the symbols *, , and * show a P value of <0.05, <0.01, and <0.001, respectively, in the agent-administered group compared to the agent-nonadministered group (Dunnett's test).
Figure 3:
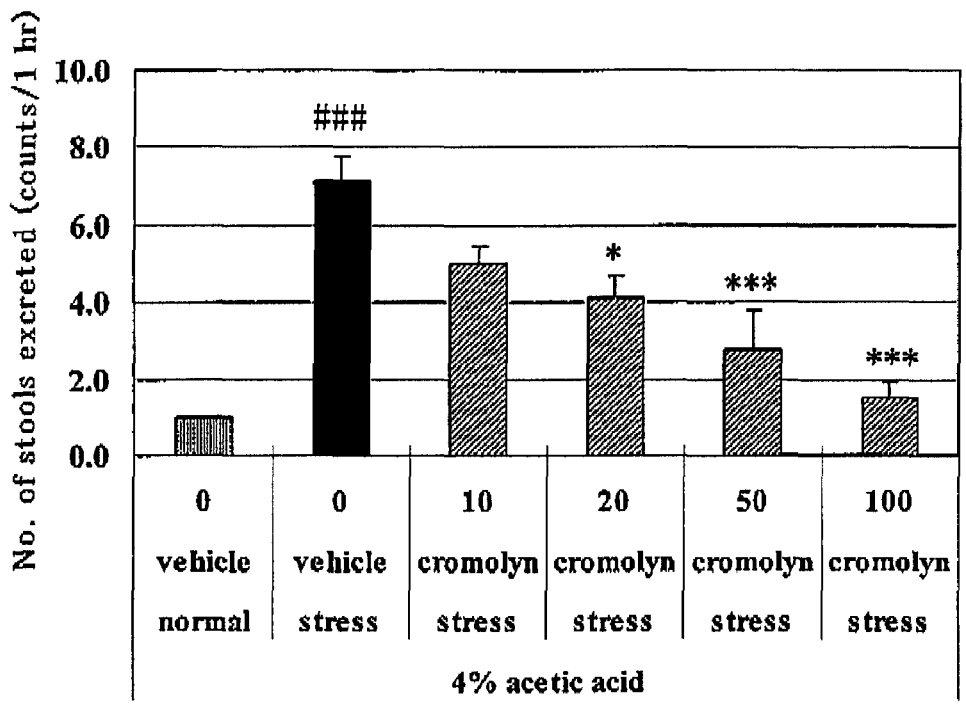
FIG. 3 is a graph showing effects of cromolyn on restraint stress-induced defecation in the acetic acid-induced IBS model in Example 2 (N=8 to 10). The ordinate axis in the graph shows the number of stools excreted for 1 hour after the initiation of restraint stress. The dosage units on the abscissa axis are all mg/kg. The symbol ### shows a P value of <0.001 in the restrained group compared to the unrestrained group (Student's t-test), and the symbols * and *** show a P value of <0.05 and <0.001, respectively, in the agent-administered group compared to the agent-nonadministered group (Dunnett's test).
Figure 4:
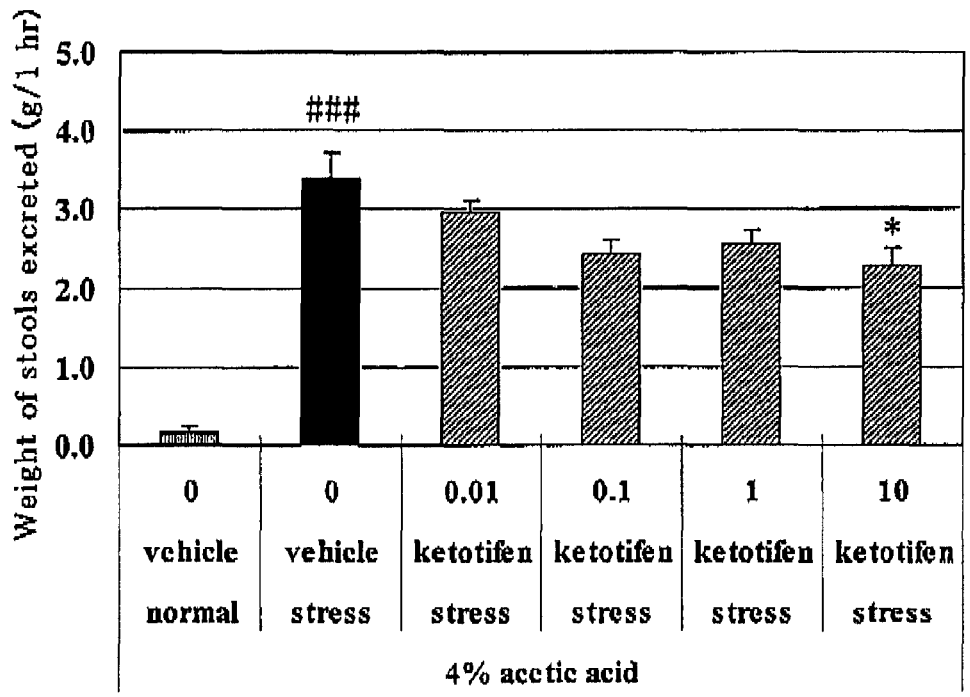
FIG. 4 is a graph showing effects of ketotifen on restraint stress-induced defecation in the acetic acid-induced IBS model in Example 2 (N=6 to 10). The ordinate axis in the graph shows the number of stools excreted for 1 hour after the initiation of restraint stress. The dosage units on the abscissa axis are all mg/kg. The symbol ### shows a P value of <0.001 in the restrained group compared to the unrestrained group (Student's t-test), and the symbol * shows a P value of <0.05 in the agent-administered group compared to the agent-nonadministered group (Dunnett's test).

Cromolyn was used by dissolving it in physiological saline, and compound 1 and ketotifen were used by dissolving them in 0.5% methylcellulose aqueous solution, respectively. Each compound was intraperitoneally administered (cromolyn) or orally administered (compound 1 and ketotifen) to male SD rats under no fasting at 7 days after the 4% acetic acid treatment or physiological saline treatment. The animals were put into restraint stress cages (product name: KN-468 (B), mfd. by Natsume Seisakusho) 30 minutes thereafter and the number and weight of the stools excreted for 1 hour were measured ("stress"). On the other hand, the normal group was put into individual cage and the number and weight of the stools excreted for 1 hour were measured in the same manner ("normal"). Results of the restraint stress-induced defecation in the agent-nonadministered group are shown in FIG. 1, and the results of agent-administered groups in FIGS. 2 to 4 respectively. As shown in FIGS. 2 and 3, compound 1 and cromolyn showed inhibitory effects on restraint stress-induced defecation in a dose-dependent manner and inhibited it almost completely at 1 mg/kg, po and 100 mg/kg. ip, respectively. On the other hand, ketotifen showed only about 30% of the inhibitory effects at the maximum (FIG. 4). When calculated from the above results, 50% inhibitory doses ($ED_{50}$ values) of compound 1 and cromolyn for restraint stress-induced defecation in the acetic acid-induced IBS model were 0.0071 mg/kg, po and 19.9 mg/kg, ip, respectively (Table 1).

In addition, the inhibitory effects of compound 1 and cromolyn on the release of histamine by an antigen-antibody reaction using rat abdominal mast cells were measured by a fluorescent method which is a modified method of Shore et al. (*The Journal of Pharmacology and Experimental Therapeutics*, 1959, vol. 127, pp. 182-186) with o-phthalaldehyde. As a result, their 50% inhibitory concentrations ($IC_{50}$ values) were 0.0074 µg/ml and 2.2 µg/ml, respectively (Table 1).

TABLE 1

|  | Restraint stress-induced defecation ($ED_{50}$ mg/kg) | Degranulation (mast cells) ($IC_{50}$ µg/ml) |
| --- | --- | --- |
| Compound 1 | 0.0071 | 0.0074 |
| Cromolyn | 19.9 | 2.2 |
| Ratio (Cromolyn/Compound 1) | 2800 | 297 |

As shown in Table 1, it was confirmed that compound 1 has an inhibitory effect on restraint stress-induced defecation, which is far stronger in comparison with cromolyn than the case predicted from its inhibitory activity on mast cell degranulation.

Example 3

Figure 5:
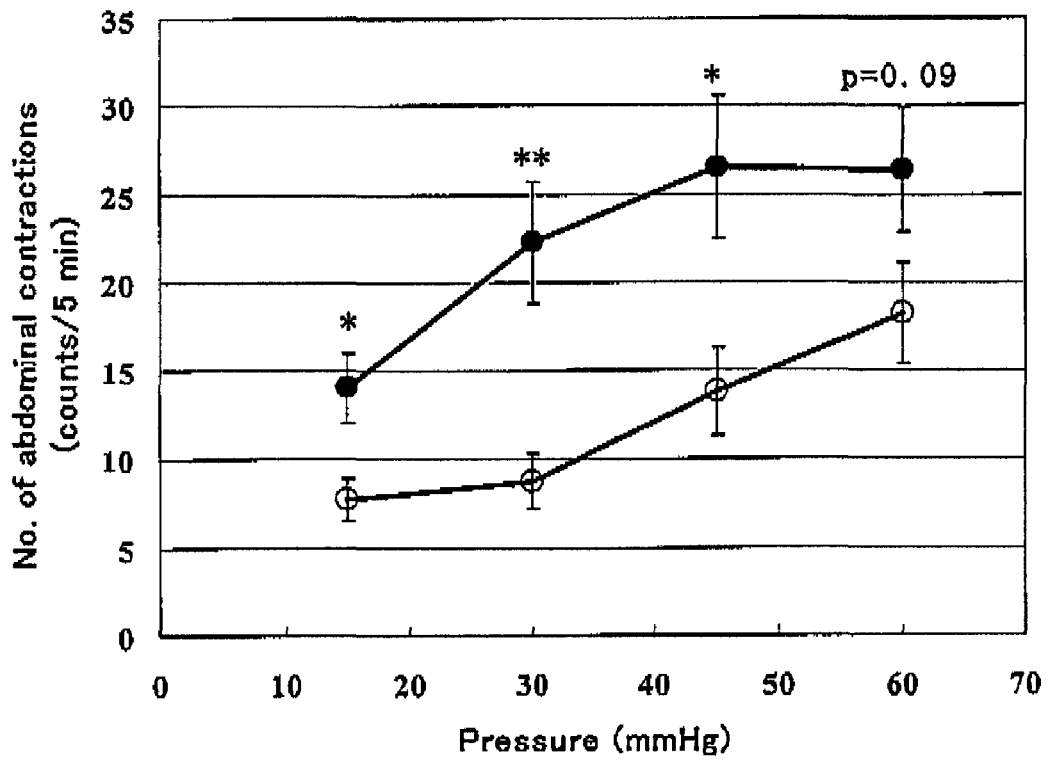
FIG. 5 is a graph showing viscerosensory response to colorectal distention in the acetic acid-induced IBS model of the drug-nonadministered group in Example 3 (N=12, the open circles show the physiological saline-treated group, and the closed circles show the 4% acetic acid-treated group). The ordinate axis in the graph shows the number of abdominal contractions per 5 minutes period during colorectal distention. The abscissa axis shows balloon internal pressure. The symbols * and ** show a P value of <0.05 and <0.01, respectively, in the 4% acetic acid group compared to the physiological saline-treated group (Student's t-test).

Viscerosensory Response to Colorectal Distention with Evaluation of the Number of Abdominal Contractions as the Index Cromolyn was used by dissolving it in physiological saline, and compound 1, alosetron and ramosetron were used by dissolving them in 0.5% methylcellulose aqueous solution, respectively. Male Wistar rats under no fasting at 7 days after 4% acetic acid treatment or physiological saline treatment were used. Under light ether anesthesia, a latex balloon of 6 cm in length was inserted intra-anally until the end of the balloon was 2 cm inside the rectum. The catheter connecting from the balloon was fixed to the tail base with a tape and connected to a pressure transducer via a three-way cock. After restoration from the ether anesthesia in a cage (23.5×19×19 cm), nociceptive behavior (the number of abdominal contractions) to colorectal distention (15, 30, 45, 60 mmHg) applied stepwise at 5 minute intervals was measured. As shown in FIG. 5, significant viscerosensory response was observed in the 4% acetic acid-treated group in comparison with the saline-treated group. In this connection, each compound was administered 30 minutes before the colorectal distention.

Figure 6:
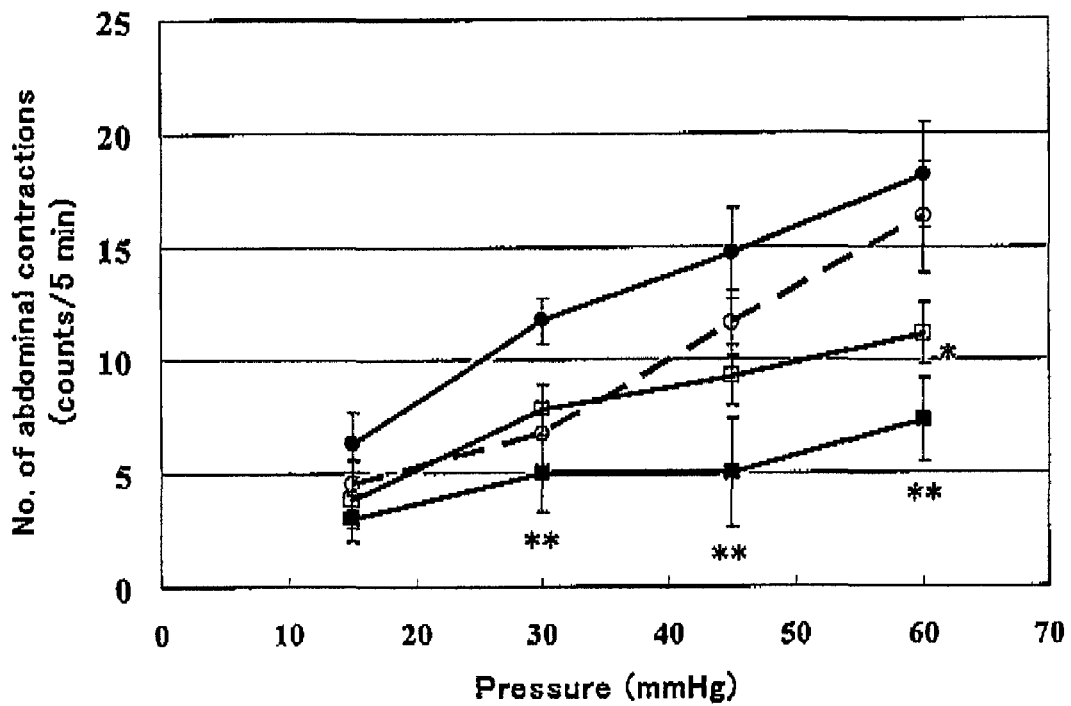
FIG. 6 is a graph showing effects of compound 1 on the viscerosensory response in the acetic acid-induced IBS model in Example 3 (N=6 to 8). The open circles show the physiological saline-treated group, the closed circles show the 4% acetic acid-treated group, the open squares show 4% acetic acid+compound 1 (0.01 mg/kg, po)-treated group, and the closed squares show 4% acetic acid+compound 1 (1 mg/kg, po)-treated group. In this connection, the ordinate axis in the graph shows the number of abdominal contractions per 5 minutes period during colorectal distention, and the abscissa axis shows the balloon internal pressure. The symbols * and ** show a P value of <0.05 and <0.01, respectively, in the agent-administered group compared to agent-nonadministered group in the 4% acetic acid-treated rats (Dunnett's test).

Results for compound 1 are shown in FIG. 6. As shown in FIG. 6, compound 1 showed dose-dependent inhibitory effects on the abdominal contractions caused by the colorectal distention, so that it was suggested that it also shows improving effects on the abdominal pain of IBS.

Figure 7:
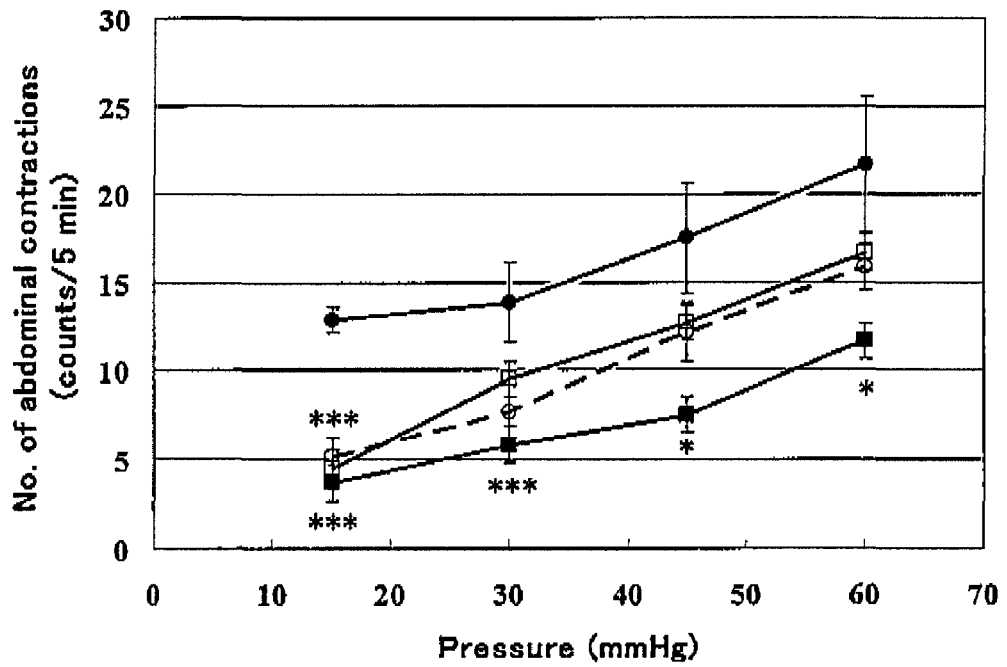
FIG. 7 is a graph showing effects of the concomitant use of compound 1 and ramosetron on the viscerosensory response in the acetic acid-induced IBS model in Example 3 (N=6, the open circles show the physiological saline-treated group, the closed circles show the 4% acetic acid-treated group, the open squares show the 4% acetic acid+ramosetron (0.01 mg/kg, po)-treated group, and the closed squares show the 4% acetic acid+compound 1 (0.01 mg/kg, po)+ramosetron (0.01 mg/kg, po)-treated group). The ordinate axis in each graph shows the number of abdominal contractions per 5 minutes period during colorectal distention, and the abscissa axis shows the balloon internal pressure. The symbols * and *** show a P value of <0.05 and <0.001, respectively, in the agent-administered group compared to the agent-nonadministered group in the acetic acid-treated rats (Student's t-test).
Figure 8:
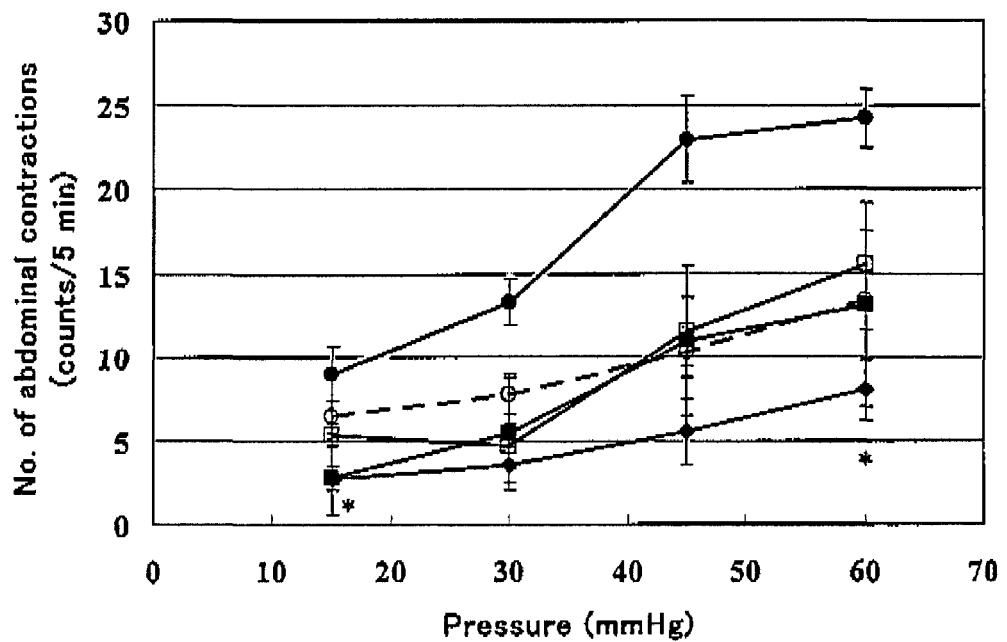
FIG. 8 is a graph showing effects of the concomitant use of compound 1 or cromolyn and alosetron on the viscerosensory response in the acetic acid-induced IBS model in Example 3 (N=6 to 12, the open circles show the physiological saline-treated group, the closed circles show the 4% acetic acid-treated group, the open squares show the 4% acetic acid+alosetron (0.1 mg/kg, po)-treated group, the closed squares show the 4% acetic acid+alosetron (0.1 mg/kg, po)+cromolyn (20 mg/kg, ip)-treated group, and the closed diamond shows the 4% acetic acid+alosetron (0.1 mg/kg, po)+compound 1 (0.01 mg/kg, po)-treated group). The ordinate axis in the graph shows the number of abdominal contractions per 5 minutes period during colorectal distention, and the abscissa axis shows the balloon internal pressure. The symbol * shows a P value of <0.05 in the compound-1-concomitantly treated group compared to alosetron-single-treated group in the acetic acid-treated rats (Student's t-test).

In addition, by using cromolyn (20 mg/kg, ip), compound 1 (0.01, 1 mg/kg, po), alosetron (0.1 mg/kg, po) and ramosetron (0.01 mg/kg, po), the results of the concomitant use of compound 1 and ramosetron are shown in FIG. 7, and those of the concomitant use of compound 1 and alosetron and the concomitant use of cromolyn and alosetron are sown in FIG. 8. In addition, it was confirmed that alosetron and ramosetron show maximal inhibitory effects on abdominal contractions at the above doses.

As a result, compound 1 showed the inhibitory effects on abdominal contractions additively with ramosetron and alosetron, but reinforcement of the effect was not found by cromolyn.

Example 4

Spontaneous Defecation in Mice

Doxantrazole was used by dissolving it in 5% (w/v) $NaHCO_3$ aqueous solution, and compound 1 was used by dissolving it in 0.5% methylcellulose aqueous solutions Male ddY mice under no fasting were reared in individual cages from the evening of the previous day of the experiment. On the day of the experiment, each compound was administered intraperitoneally (doxantrazole) or orally (compound 1), and the number of stools spontaneously excreted for 2 hours after the initiation of the experiment was measured.

Figure 9A:
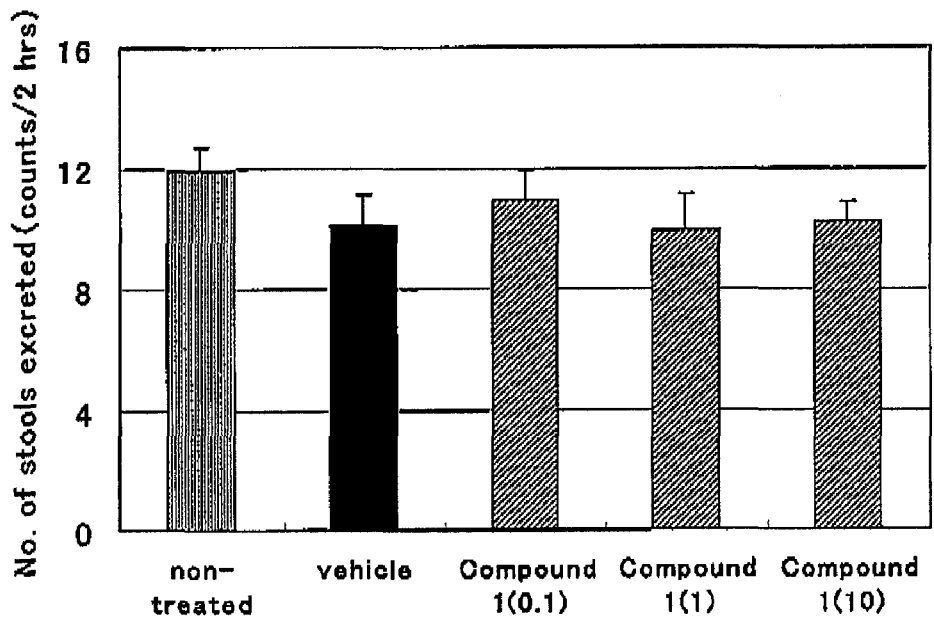
FIGS. 9A and 9B are graphs showing effects of compound 1 and doxantrazole on spontaneous defecation in mice in Example 4.
Figure 9B:
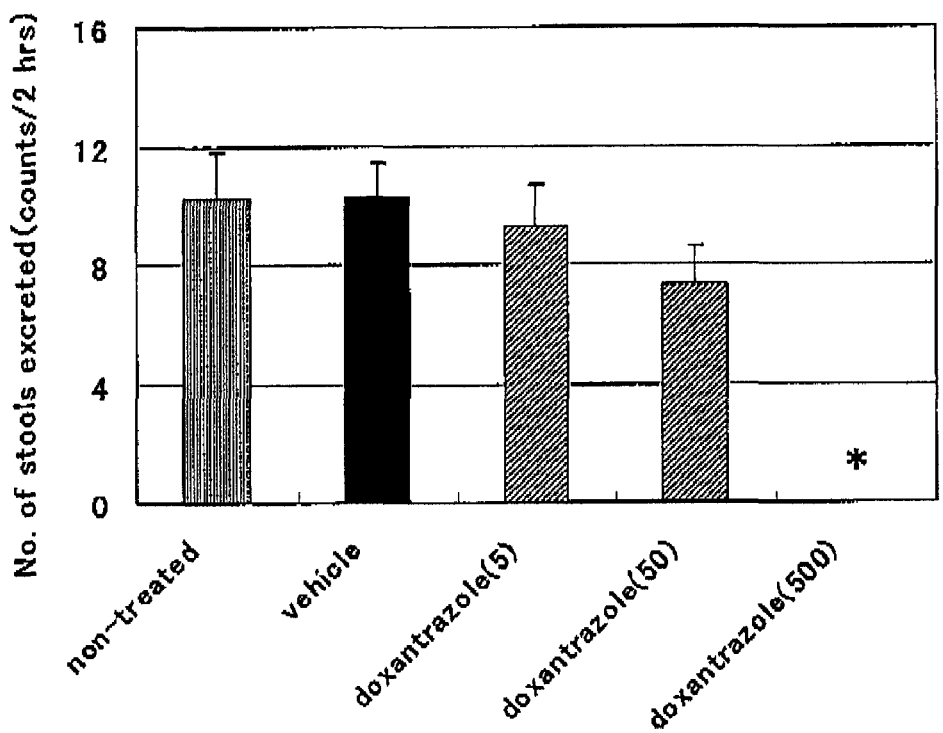

The results are shown in FIGS. 9A and 9B. As shown in FIG. 9A, compound 1 showed no effect on the spontaneous defecation in mice, while doxantrazole showed an inhibitory tendency on the spontaneous defecation in mice as shown in FIG. 9B. In addition, death of all cases was found for doxantrazole in the 500 mg/kg administration group.

As the results of the aforementioned respective experiments, it was confirmed that N-(1H-tetrazol-5-yl)-1-phenoxy-4H-quinolizin-4-one-3-carboxamide has the effect of improving altered bowel motility and abdominal symptom in IBS, and it is evident that its effect is far stronger than those predicted from other mast cell degranulation inhibitors, and further that it can become a safe IBS-treating agent which does not cause the inhibitory effect on spontaneous defecation in normal animals.

In addition, when used concomitantly with a 5-HT3 receptor antagonist, N-(1H-tetrazol-5-yl)-1-phenoxy-4H-quinolizin-4-one-3-carboxamide shows the ability to alleviate bowel-related symptoms and abdominal symptoms in IBS, which cannot be inhibited by one agent alone, so that a pharmaceutical preparation consisting of a combination thereof is also useful as an IBS-treating agent.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A method for treating irritable bowel syndrome, which comprises administering an effective amount of N-(1H-tetrazol-5-yl)-1-phenoxy-4H-quinolizin-4-one-3-carboxamide or a pharmaceutically acceptable salt thereof, to a patient in need thereof.

2. The method of claim 1, which comprises administering an effective amount of N-(1H-tetrazol-5-yl)-1-phenoxy-4H-quinolizin-4-one-3-carboxamide sodium salt monohydrate to said patient in need thereof.

3. The method of claim 2, wherein said irritable bowel syndrome is irritable bowel syndrome with diarrhea.

4. The method of claim 2, wherein said irritable bowel syndrome is irritable bowel syndrome with constipation.

5. The method of claim 2, wherein said irritable bowel syndrome is mixed irritable bowel syndrome.

6. The method of claim 1, wherein said irritable bowel syndrome is irritable bowel syndrome with diarrhea.

7. The method of claim 1, wherein said irritable bowel syndrome is irritable bowel syndrome with constipation.

8. The method of claim 1, wherein said irritable bowel syndrome is mixed irritable bowel syndrome.

9. A method for treating irritable bowel syndrome, which comprises administering an effective amount of N-(1H-tetrazol-5-yl)-1-phenoxy-4H-quinolizin-4-one-3-carboxamide or a pharmaceutically acceptable salt thereof and at least one 5-HT3 receptor antagonist to a patient in need thereof.

10. The method of claim 9, which comprises administering an effective amount of N-(1H-tetrazol-5-yl)-1-phenoxy-4H-quinolizin-4-one-3-carboxamide sodium salt monohydrate to said patient in need thereof.

11. The method of claim 10, wherein said irritable bowel syndrome is irritable bowel syndrome with diarrhea.

12. The method of claim 10, wherein said irritable bowel syndrome is irritable bowel syndrome with constipation.

13. The method of claim 10, wherein said irritable bowel syndrome is mixed irritable bowel syndrome.

14. The method of claim 9, wherein said irritable bowel syndrome is irritable bowel syndrome with diarrhea.

15. The method of claim 9, wherein said irritable bowel syndrome is irritable bowel syndrome with constipation.

16. The method of claim 9, wherein said irritable bowel syndrome is mixed irritable bowel syndrome.

17. The method of claim 9, wherein said at least one 5-HT3 receptor antagonist is at least one member selected from the group consisting of ramosetron, alosetron, and a mixture thereof.

18. The method of claim 9, which comprises administering N-(1H-tetrazol-5-yl)-1-phenoxy-4H-quinolizin-4-one-3-carboxamide sodium salt monohydrate and at least one member selected from the group consisting of ramosetron, alosetron, and a mixture thereof.

19. The method of claim 9, which comprises administering N-(1H-tetrazol-5-yl)-1-phenoxy-4H-quinolizin-4-one-3-carboxamide sodium salt monohydrate and ramosetron.

20. The method of claim 9, which comprises administering N-(1H-tetrazol-5-yl)-1-phenoxy-4H-quinolizin-4-one-3-carboxamide sodium salt monohydrate and alosetron.

* * * * *